(12) United States Patent
Edge

(10) Patent No.: US 6,284,245 B1
(45) Date of Patent: Sep. 4, 2001

(54) NEURAL RETINAL CELLS AND RETINAL PIGMENT EPITHELIUM CELLS AND THEIR USE IN TREATMENT OF RETINAL DISORDERS

(75) Inventor: Albert Edge, Cambridge, MA (US)

(73) Assignee: Diacrin, Inc., Charlestown, MA (US)

( * ) Notice: Subject to any disclaimer, the term of this patent is extended or adjusted under 35 U.S.C. 154(b) by 0 days.

(21) Appl. No.: 09/139,812

(22) Filed: Aug. 25, 1998

(51) Int. Cl.$^7$ .................................................. C12N 5/06
(52) U.S. Cl. ................................. 424/93.7; 435/1.1
(58) Field of Search ............................. 424/93.7; 435/1.1

(56) References Cited

U.S. PATENT DOCUMENTS

| | | | |
|---|---|---|---|
| 5,202,120 | * 4/1993 | Silver et al. | 424/93 |
| 5,629,194 | * 5/1997 | Dinsmore | 435/325 |
| 5,679,340 | * 10/1997 | Chappel | 424/93.1 |

FOREIGN PATENT DOCUMENTS

| | | |
|---|---|---|
| WO 93/08848 | 5/1993 | (WO) . |
| WO 95/33828 | 12/1995 | (WO) . |
| WO 96/14399 | 5/1996 | (WO) . |

OTHER PUBLICATIONS

De Shaepdrijver et al., Anatomia Histologia Embryologia 19(3):222–235 (Sep. 1990). (Abstract).*

Sharma, Rajesh K. and Ehinger, Berndt (1997) "Cell Proliferation In Retinal Transplants", Cell Transportation, vol. 6, No. 2, p. 141–148.

Sharma, Rajesh K. and Ehinger, Berndt (1996) "Proliferation of Cells In Developing Rabbit Retina" Investigative Ophthalmology & Visual Science, vol. 37, No. 3, Abstract No. 3162.

Berger et. al., (1996) "Harvest of adult human photoreceptor tissue for retinal transplantation" Investigative Ophthalmology & Visual Science. vol. 37 p S95. Abstract 456–B368.

Berger et al., (1997) "Long–term culture of adult human retinal pigment epithelium (RPE) and choroid" Investigative Ophthalmology & Visual Science vol. 38 p S946 Abstract 4390.

Berglin, L., et al. (1997) "Tolerance of human fetal retinal pigment epithelium xenografts in monkey retina" Graefe's Arch. Clin. Exp. Ophthalmol., vol. 235 pp. 103–110.

del Cerro., M. et al. (1995) "Viability of optisol–stored human fetal neural retina: an in vivo and graft survival study." Investigative Ophthalmology & Visual Science. vol. 36 p. S254, Abstract 1154–102.

del Cerro., M. et al. (1996) "Fetal neural retinal grafts into human retinitis pigmentosa" Society for Neuroscience. vol 22 p. 319. Abstract 131.12.

del Cerro, M., et al. (1992) "Intraretinal xenografts of differentiated human retinoblastoma cells integrate with host retina" Brain Research. vol. 583 pp 12–22.

(List continued on next page.)

*Primary Examiner*—Jean C. Witz
(74) *Attorney, Agent, or Firm*—Lahive & Cockfield LLP; Megan E. Williams, Esq.; Amy E. Mandragouras, Esq.

(57) ABSTRACT

Compositions comprising porcine retinal cells and methods for using the compositions to treat retinal disorders are described. The porcine retinal cells are preferably fetal neural retina cells or retinal pigment epithelial cells. The porcine retinal cells can be modified to be suitable for transplantation into a xenogeneic subject, such as a human. For example, the porcine retinal cells can be modified such that an antigen (e.g., an MHC class I antigen) on the cell surface which is capable of stimulating an immune response against the cell in a xenogeneic subject is altered (e.g., by contact with an anti-MHC class I antibody, or a fragment or derivative thereof) to inhibit rejection of the cell when introduced into the subject. In one embodiment, the porcine retinal cells are obtained from a pig predetermined to be free from organisms which originate in pig and which are capable of transmitting infection or disease to the recipient subject. The porcine retinal cells of the present invention can be used to treat a xenogeneic subject having a retinal disorder (e.g., a human with retinis pigmentosa, light damaged retina and macular degeneration by introducing the cells into the retina of the subject.

17 Claims, No Drawings

OTHER PUBLICATIONS del Cerro, M., et al. (1992) "Photoreceptor differentiation in retinal xenografts of fetal monkey retina" Brain Research. vol. 574 pp. 1–8.

DiLoreto, D. et al. (1997) "Fluoroscein as a marker for subretinal ttransplantation of human fetal neural retina" Current Eye Research. vol. 16 pp 1159–1165.

DiLoreto, D., et al. (1996) "Cyclosporine treatment promotes survival of human fetal neural retina transplanted to the subretinal space of the light–damaged Fischer 344 rat" Experimental Neurology. vol. 140 pp 37–42.

DiLoreto, D. et al. (1996) "Cyclosporine immunosuppression promotes survival of human fetal neural retina transplanted to the subretinal space of the light damaged Fischer 344 rat" Investigative Ophthalmology & Visual Science. vol. 37 p S95. Abstract 452–B364.

Del Priore, L.V. et al. (1995) "Debridement of the pig retinal pigment epithelium in vivo" Arch. Ophthalmol. vol. 113 pp 939–944.

Del Priore, L.V. et al. (1988) "Morphology of pig retinal pigment epithelium maintained in organ culture" Arch Ophthalmol. vol. 106 pp 1286–1290.

Duru, Y.K. and Tamai, M. (1997) "Transplantation of retinal pigment epithelium using viable cryopreserved cells" Cell Transplantation. vol. 6 pp 149–162.

Edwards, R.B. (1982) "Culture of mammalian retinal pigment epithelium and neural retina" Methods in enzymology. vol. 81 pp 39–43.

Epstein, et al. (1994) Human neural xenografts: progress in developing an in–vivo model to study human immunodeficiency virus (HIV) and human cytomegalovirus (HCMV) infection. vol. 4 pp 257–260.

Gouras, P. et al. (1996) "Human Fetal RPE Xenografts in Monkey Retina" Investigative Ophthalmology & Visual Science, vol. 37, No. 3, p. S95, Abstract 451–B363.

Gouras, P. et al. (1994) "Patch Culturing and Transfer of Human Fetal Retinal Epithelium" Graefe's Arch Clin Exp Ophthalmol, vol. 232, pp. 599–607.

Jones, Z. et al. (1997) "Definitive Identification of Transplanted Porcine Retinal Pigment Epithelium (RPE) With Barr Body Staining" Investigative Ophthalmology & Visual Science, vol. 38, No. 4, p. S336, Abstract 1572–B365.

Li, Linxi and Turner, James E. (1991) "Optimal Conditions for Long–term Photoreceptor Cell Rescue in RCS Rats: The Necessity for Healthy RPE Transplants" Exp. Eye Res., vol. 52, pp. 669–679.

Little, C.W. et al. (1997) "Water Escape as a Tool to Demonstrate Functional Advantage Following Retinal Transplantation" Investigative Ophthalmology & Visual Science, vol. 38, No. 4, p. S335, Abstract 1565–B358.

Little, C.W. et al. (1996) "Transplantation of Human Fetal Retinal Pigment Epithelium Rescues Photoreceptor Cells From Degeneration in the Royal College of Surgeons Rat Retina" Investigative Ophthalmology & Visual Science, vol. 37, No. 1, pp. 204–211.

Pomeranz, H.D. et al. (1995) "Porcine Retinal Pigment Epithelium (RPE) Attachment and Growth on RPE Extracellular Matrix in Vitro" Investigative Ophthalmology & Visual Science, vol. 36, No. 4, p. S766, Abstract 3538–525.

Reh, Thomas A. (1992) "Cellular Interactions Determine Neuronal Phenotypes in Rodent Retinal Cultures" Journal of Neurobiology, vol. 23, No. 8, pp 1067–1083.

Sharma, Rajesh K. and Ehinger, Berndt (1997) "Retinal Cell Transplants: How Close to Clinical Application?" Acta Ophthalmol. Scand., vol. 75, pp. 355–363.

Sheedlo, Harold J. and Turner, James E. (1996) "Influence of a Retinal Pigment Epithelial Cell Factor(s) on Rat Retinal Progenitor Cells" Developmental Brain Research, vol. 93, pp. 88–99.

Sheng, Y. et al. (1995) "Patch Transplants of Human Fetal Retinal Pigment Epithelium in Rabbit and Monkey Retina" Investigative Ophthalmology & Visual Science, vol. 36, No. 2, pp. 381–390.

Tezel, Tongalp H. and Del Priore, Lucian V. (1996) "Density–dependent Growth Regulation of Pig Retinal Pigment Epithelial Cells In Vitro" Graefe's Arch Clin. Exp. Ophthalmol., vol. 234, pp. S89–S90.

Ho, Tzyy–Chang et al. (1997) "Tissue Culture of Retinal Pigment Epithelium Following Isolation with a Gelatin Matrix Technique" Exp. Eye Res., vol. 64, pp. 133–139.

Vollmer, Günter and Layer, Paul G. (1986) "An in vitro Model of Proliferation and Differentiation of the Chick Retina: Coaggregates of Retinal and Pigment Epithelial Cells" The Journal of Neuroscience, vol. 6, No. 7, pp. 1885–1896.

Jones, Z. et al, "Definitive Identification of Transplanted Porcine Retinal Pigment Epithelium (RPE) with Barr Body Staining," Investigative Ophthalmology & Visual Science vol. 38, No. 4: p. 1572, Mar. 1997.*

Gaudin, C. et al, "Survival and Regeneration of Adult Human and Other Mammalian Photoreceptors in Culture," Investigative Ophthalmology & Visual Science vol. 37, No. 11: pp. 2258–2268, Oct. 1996.*

Schraermeyer, U. et al, "Porcine Iris Pigment Epithelial Cells Can Take Up Retinal Outer Segments," Experimental Eye Research vol. 65, No. 1: pp. 277–287, Aug. 1997.*

* cited by examiner

NEURAL RETINAL CELLS AND RETINAL PIGMENT EPITHELIUM CELLS AND THEIR USE IN TREATMENT OF RETINAL DISORDERS

BACKGROUND OF THE INVENTION

Macular degeneration is a disease of the retina which affects over thirteen million people in the United States and is characterized by loss of central vision due to the loss of photoreceptors in the central part of the retina, the macula lutea. D'Amico et al. (1994) New England J. Med. 331:95–106 and Kliffen et al. (1997) Microscopy Res. & Techniq. 36:106–122. The macula is the most important part of the eye for high resolution vision because there is a greater concentration of cone type photoreceptors which are responsible for color vision and visual acuity.

Photoreceptor cells, especially rod cells, renew their outer segments at a high rate. Thus, as new lamellae discs are formed and added to the photoreceptor cells, the older lamellae discs at the tip are discarded. Retinal pigment epithelial (RPE) cells function to provide support for the retinal photoreceptors and are responsible for the metabolic digestion of the discarded outer segments of the neural retina. Thus, RPE cells are responsible for the phagocytosis and digestion of the discarded discs at a turn over rate of approximately 30–100 discs each day. Underlying the RPE cells is the choriocapillaris which contains the vasculature to provide nutrients and remove metabolic by-products from the retina.

In macular degeneration, the RPE cells are dysfunctional, thereby leading to a build up of metabolic by-products, including discarded discs in the retina. The presence of metabolic debris and excess fluid in the retina damage photoreceptor cells, thereby compromising visual acuity. Cingle et al. (1996) Curr. Eye. Res. 15:433–438 and Curcio et al. (1996) Invest. Ophthal. & Vis. Sci. 37:1236–1249. In addition, the degeneration of the RPE layer is also reflected by ensuing atrophy of the choriocapillaris.

In the dry form of macular degeneration, loss of vision is gradual and is associated with retinal pigment changes, deposits in the subretinal space called drusen, atrophy of the blood vessels supplying the retina and ultimately geographic atrophy in the absence of neovascularization. Although this form of macular degeneration has a slower progression to blindness, it is far more common, accounting for approximately 90% of the cases of acute macular degeneration. In the wet form of the disease, vessels arise from the choriocapillaris and penetrate Bruch's membrane and the RPE cell layer to impinge upon the neural retina where they cause damage that leads to loss of central vision. Patients with the wet form of the disease are at high risk for subretinal neovascularization, geographic atrophy and retinal pigment epithelial detachment, all of which result in a rapid and severe loss of visional acuity.

Currently, there are few therapeutic alternatives for patients diagnosed with macular degeneration. Laser photocoagulation has been used for some cases of the wet form of the disease, but the clinical experience with this therapy has not been promising. If the retinal damage is close to the fovea, laser therapy is withheld to avoid potential loss of central photoreceptors. Lambert et al. (1992) Am. J. Ophthalmol. 113:257–262. In addition, radiation and photodynamic therapy has been performed for cases where neovascularization is diffuse or too severe. Although follow-up data showed an advantage of laser photocoagulation, reoccurrence of neovascularization occurred in over half of the patients, thereby undermining the initial benefit of the treatment. Macular Photocoagulation Study Group (1993) Arch. Ophthalmol. 111:1200–1209.

Opthalmic surgery can also be performed to remove neovascularization in the wet form of macular degeneration. Although this surgery has been reported to reduce the progression of the disease, restoration of visual acuity is limited.

The other competitive approach to treating macular degeneration is surgical implantation of human RPE cells. Although early clinical analysis has been promising, broader clinical application of human transplants to patients with macular degeneration will be extremely limited by the availability of human donors. Thus, a need exists for alternative sources of retinal cells and methods of retinal transplantation which can minimize the damage caused by retinal disorders such as macular degeneration.

SUMMARY OF THE INVENTION

The instant invention pertains to an isolated retinal cell or an isolated population of retinal cells suitable for transplantation into an allogeneic or xenogeneic subject, particularly a human subject. The retinal cells of the invention include neural retinal cells (e.g., rod or cone photoreceptor cells), retinal pigment epithelial (RPE) cells, iris epithelial cells and retinal stem cells (e.g., retinal progenitor cells). Thus, one aspect of the invention pertains to a transplantable composition for use in a subject comprising a retinal cell (e.g., a neural retina cell, RPE cell or iris epithelial cell) obtained from a pig, e.g., a fetal pig.

The porcine retinal cells of the invention include porcine neural retinal cells, retinal pigment epithelial (RPE) cells, iris epithelial cells and their precursors. Typically, these retinal cells are obtained from fetal pigs during selected stages of gestational development. For example, it has been determined that fetal retinal cells obtained from a fetal pig between about days 30 and 100, more preferably about days 40 and 90, and still more preferably about days 50 and 80, and yet more preferably about days 60 and 70, and most preferably about day 60–65 of gestation are suitable for transplantation into xenogeneic subjects, particularly human subjects.

Another aspect of the invention pertains to a porcine retinal cell or a population of retinal cells which are obtained from a pig predetermined to be free from at least two organisms which originate in pigs and which are capable of transmitting infection or disease to a xenogeneic recipient, e.g., a human, of the cells.

Categories of organisms from which the cells are free can include zoonotic, cross-placental, neurotropic, and/or ocular-infecting organisms. Within each of these categories, the organism can be a parasite, bacteria, mycoplasma, and/or a virus. In one embodiment, the retinal cells are free of one or more of the following organisms found in pigs: Toxoplasma, eperythrozoon, brucella, listeria, mycobacterium TB, leptospirillum, hemophilus suis, M. Hypopneumonia, porcine respiratory reproductive syndrome, rabies, pseudorabies, parvovirus, encephalomyocarditis virus, swine vesicular disease, teschen (Porcine polio virus), hemagglutinating encephalomyocarditis, suipoxvirus, swine influenza type A, adenovirus, transmissible gastroenteritis virus, bovine viral diarrhea, and vesicular stomatitis virus.

In another aspect of the invention, the retinal cell, in unmodified form, has at least one antigen on the cell surface which is capable of stimulating an immune response against the cell in a xenogeneic subject, for example, a human. The antigen on the surface of the retinal cell is altered to inhibit rejection of the cell when introduced into a xenogeneic subject. In one embodiment, the cell surface antigen which is altered is an MHC class I antigen. This MHC class I antigen can be contacted, prior to transplantation into a xenogeneic subject with at least one anti-MHC class I antibody, or a fragment or derivative thereof, which binds to the MHC class I antigen on the cell surface but does not activate complement or induce lysis of the cell. One example of an anti-MHC class I antibody is an anti-MHC class I F(ab')$_2$ fragment, such as an anti-MHC class I F(ab')$_2$ fragment of a monoclonal antibody PT85. The retinal cells can further be screened as described above such that the cells are isolated from a pig predetermined to be essentially free of organisms which are capable of being transmitted to a xenogeneic subject, e.g., a human subject.

Another aspect of the invention features a composition comprising a porcine retinal cell, e.g., a porcine neural retina cell, RPE cell or iris epithelial cell, and an antibody which binds an antigen on the surface of the porcine retinal cell. The composition can further comprise a pharmaceutically acceptable carrier.

This invention also provides methods for treating a retinal disorder in a subject by administering to the subject having the disorder a composition comprising the retinal cells of the invention, e.g., neural retina cells, RPE cells or iris epithelial cells, into the retina of the subject.

In one embodiment, the retinal disorder of a subject, e.g., a human, is treated by administering to the subject a composition comprising a porcine neural retina cell into the retina, e.g., subretinal space, of the subject. The method can be used to treat retinal disorders such as retinis pigmentosa, phototoxic retinopathy, light damaged retina or macular degeneration. In another embodiment, the retinal disorder of a subject, e.g., a human, is treated by administering to the subject a composition comprising a porcine RPE cell into the retina, e.g., subretinal space, of the subject. This method can be used to treat retinal disorders such as macular degeneration, gyrate atrophy, fundus flavimaculatus, Best's disease, Sorsby's dystrophy or Stargardt's disease. The RPE cells can be administered to the subject in a cell suspension or can be administered as an intact sheet.

The compositions of the invention can further comprise a pharmaceutically acceptable carrier. In one embodiment, the porcine retinal cells, e.g., neural retinal cells, RPE cells or iris epithelial cells, which can be administered to a subject having a retinal disorder are porcine retinal cells which, in unmodified form, have at least one antigen on the cell surface which is capable of stimulating an immune response against the cell in a subject, e.g., a xenogeneic subject, e.g., a human. The antigen on the surface of the porcine retinal cell is altered to inhibit rejection of the cell when introduced into the subject. Examples of retinal cell surface antigens and methods of altering such antigens are described herein. Preferred retinal cell ages are also described herein. In another embodiment, the porcine retinal cells which can be administered to a subject having a retinal disorder are porcine retinal cells, e.g., neural retina cells, RPE cells or iris epithelial cells, which are obtained from a pig predetermined to be free from at least two organisms which originate in pig and which are capable of transmitting infection or disease to a xenogeneic recipient, e.g., a human, of the cells. Pathogen-free pigs are described in detail herein.

Other features and advantages of the invention will be apparent from the following detailed description and claims.

DETAILED DESCRIPTION OF THE INVENTION

I. Isolated Cells and Cell Populations of the Invention

This invention features retinal cells suitable for introduction into an allogeneic or xenogeneic recipient, particularly a human subject. As used herein the phrase "retinal cell" includes neural retinal cells (also referred to herein as photoreceptor cells), retinal pigment epithelial (RPE) cells, iris epithelial cells, and their precursors. In a preferred embodiment, the retinal cells are mammalian retinal cells, e.g., porcine retinal cells or human retinal cells. The terms "precursor", "progenitor", and "stem cell" are used interchangeably herein and refer to cells which are multipotent, i.e., are capable of developing into a many different cell types, including neural retina cells, RPE cells and/or iris epithelial cells. "Retinal pigment epithelial (RPE) cells", as used herein refer to cells of the outermost external layer of the retina. RPE cells function to provide support for the retinal photoreceptors and are responsible for the metabolic digestion of the discarded outer segments of the neural retina. "Neural retina cells", as used herein, refer to the layer of photoreceptor cells (i.e., rod and cone cells) underlying the RPE cell layer in the retina. Neural retina cells are modified light sensitive neurons. Such precursor cells can be used as sources of the mammalian retinal cells of the invention, i.e., the retinal cells of the invention can be derived from such precursor cells. As used herein, the term "derived" refers to cells which develop or differentiate from or have as ancestors multipotent precursor cells. These multipotent precursor cells are typically obtained from the eye cup and are cultured in vitro as described, for example, in Sheedlo et al. (1996) *J. Neuroscience Res.* 44:519–531, the contents of which are incorporated herein by reference, to generate the cells of the present invention. Thus, in one aspect of the invention, the retinal precursor cells of the invention are induced to differentiate in vitro prior to use in the compositions of the invention.

For example, porcine fetuses can be removed from a pregnant sow at gestational ages at which the retinal cells have not committed to specific cell fates. In one embodiment, stem cells are obtained from porcine embryos in early stages of development (e.g., starting at about day 30 of gestation) and cultured under conditions which promote proliferation. Agents, e.g., retinoic acid, butyrate, triiodothyronine, basic fibroblast growth factor, transforming growth factor, and s-laminin, which promote differentiation of these stem cells into retinal cell types, e.g., such as those described herein, can then be added to the culture. The resultant differentiated retinal cells can be transplanted into a recipient subject as described herein.

A. Modified Retinal Cells and an Isolated Population of Modified Retinal Cells Retinal cells of the invention can be obtained from hemisecting the globe of the pig retina at the ora serrata and the anterior segment. Preferably, the cells are obtained from the neural retina or the eye cup of the porcine retina. In unmodified form, the retinal cell, i.e., the neural retina cell, RPE cell or iris epithelial cell, has at least one antigen on the cell surface which is capable of stimulating an immune response against the cell in an allogeneic or xenogeneic subject. To inhibit rejection of the cell when introduced into the subject, the antigen on the cell surface is altered prior to transplantation. In an unaltered state, the antigen on the cell surface stimulates an immune response against the cell when the cell is administered to a subject (also referred to herein as recipient or recipient subject). By altering the antigen, the normal immunological recognition of the retinal cell, e.g., a porcine retinal cell, by the immune system cells of the recipient is disrupted and additionally, "abnormal" immunological recognition of this altered form of the antigen can lead to retinal cell-specific long term unresponsiveness inAhe recipint. It is likely that alteration of an antigen on the retinal cell prior to introducing the cell into a subject interferes with the initial phase of recognition of the retinal cell by the cells of the host's immune system subsequent to administration of the cell. Furthermore, alteration of the antigen may induce immunological nonresponsiveness or tolerance, thereby preventing the induction of the effector phases of an immune response (e.g., cytotoxic T cell generation, antibody production etc.) which are ultimately responsible for rejection of foreign cells in a normal immune response. As used herein, the term "altered" encompasses changes that are made to at least one retinal cell antigen(s) which reduces the immunogenicity of the antigen to thereby interfere with immunological recognition of the antigen(s) by the recipient's immune system. In a preferred embodiment, at least one antigen on a porcine retinal cell, e.g., neural retina cell, RPE cell or iris epithelial cell, is altered such that upon introduction into a subject, e.g., a human, rejection of the cell is inhibited.

Antigens to be altered according to the current invention include antigens on a retinal cell, e.g., a porcine retinal cell, which can interact with an immune cell in a xenogeneic (or allogeneic) recipient subject and thereby stimulate a specific immune response against the retinal cell in the recipient. The interaction between the antigen and the immune cell may be an indirect interaction (e.g., mediated by soluble factors which induce a response in the immune cell, e.g., humoral mediated) or, preferably, is a direct interaction between the antigen and a molecule present on the surface of the immune cell (i.e., cell-cell mediated). As used herein, the term "immune cell" is intended to include a cell which plays a role in specific immunity (e.g., is involved in an immune response) or plays a role in natural immunity. Examples of immune cells include all distinct classes of lymphocytes (T lymphocytes, such as helper T cells and cytotoxic T cells, B lymphocytes, and natural killer cells), monocytes, macrophages, other antigen presenting cells, dendritic cells, and leukocytes (e.g., neutrophils, eosinophils, and basophils). In a preferred embodiment, the antigen is one which interacts with a T lymphocyte in the recipient (e.g., the antigen normally binds to a receptor on the surface of a T lymphocyte).

In one embodiment, the antigen on the retinal cell to be altered is an MHC class I antigen. Alternatively, an adhesion molecule on the cell surface, such as NCAM-1 or ICAM-1, can be altered. An antigen which stimulates a cellular immune response against the cell, such as an MHC class I antigen, can be altered prior to transplantation by contacting the cell with a molecule which binds to the antigen. A preferred molecule for binding to the antigen is an antibody, or fragment thereof (e.g., an anti-MHC class I antibody, or fragment thereof, an anti-ICAM-1 antibody or fragment thereof, an anti-LFA-3 antibody or fragment thereof, or an anti-$P_2$ microglobulin antibody or fragment thereof). A preferred antibody fragment is an $F(ab')_2$ fragment. Polyclonal or, more preferably, monoclonal antibodies can be used. Other molecules which can be used to alter an antigen (e.g., an MHC class I antigen) include peptides and small organic molecules which bind to the antigen. Furthermore, two or more different epitopes on the same or different antigens on the cell surface can be altered. A particularly preferred monoclonal antibody for alteration of MHC class I antigens on porcine retinal cells is PT85 (commercially available from Veterinary Medicine Research Development, Pullman Wash.). PT85 can be used alone to alter MHC class I antigens or, if each antibody is specific for a different epitope, PT85 can be used in combination with another antibody known to bind MHC class I antigens to alter the antigens on the cell surface. Suitable methods for altering a surface antigen on a cell for transplantation are described in greater detail in Faustman and Coe (1991) *Science* 252:1700–1702 and PCT publication WO 92/04033. Methods for altering multiple epitopes on a surface antigen on a cell for transplantation are described in greater detail in PCT publication WO 95/26741, published on Oct. 12, 1995, the contents of which are incorporated herein by reference.

In another embodiment, the porcine retinal cells of the present invention can be modified to inhibit natural antibody-mediated hyperacute rejection of the cells. For example, the retinal cells of the invention may, in unmodified form, express an epitope on their surface which stimulates hyperacute rejection of the retinal cells by natural antibodies in a recipient subject. Such an epitope can be altered, reduced or substantially eliminated. This treatment of the retinal cells inhibits subsequent recognition of the epitope by natural antibodies in a recipient, thereby inhibiting hyperacute rejection. In a preferred embodiment, the epitope is a carbohydrate, preferably galactosyl ($\alpha$1,3) galactose (Gal ($\alpha$1,3) Gal).

Epitopes on the surface of the retinal cells, e.g., neural retinal cells, RPE cells or iris epithelial cells, in one embodiment of the invention, are removed from the surface of a cell, such as by enzymatic or chemical treatment of the cell. For example, Gal ($\alpha$1,3)Gal epitopes can be cleaved from a cell surface by treatment of the cell with an alpha-galactosidase. In another embodiment, formation of the epitope on the cell surface is inhibited. This can be accomplished by inhibiting the activity of an enzyme which forms the epitope. For example, formation of Gal ($\alpha$1,3)Gal epitopes on the surface of a cell can be interfered with by inhibiting the activity of an alpha-1,3-galactosyltransferase within the cell, such as by introducing into the cell a nucleic acid which is antisense to a coding or regulatory region of an alpha-1,3-galactosyltransferase gene or by treating the cell with a chemical inhibitor of the enzyme. In yet another embodiment, epitopes on the surface of a retinal cell are altered by binding a molecule to the epitope, thereby inhibiting its subsequent recognition by natural antibodies in a recipient. For example, lectins, antibodies or antibody fragments can be bound to an epitope to inhibit its subsequent recognition by natural antibodies. Methods for altering epitopes on cell surfaces which stimulate hyperacute rejection of the cells by natural antibodies in a recipient subject are described in greater detail in PCT Publication WO/95/33828, published on Dec. 14, 1995, the contents of which are incorporated herein by reference.

The altered (also referred to herein as "modified") retinal cells can comprise an isolated population of cells. The term "population" as used herein refers to a group of two or more cells. The population of retinal cells can be neural retina cells, RPE cells and/or iris epithelial cells. In one embodiment, the population of retinal cells is a population of neural retina cells. In another embodiment, the population of retinal cells is a population of RPE cells. The population of RPE cells can be in the form of an intact sheet comprising, for example, an intact monolayer of RPE cells, or in a cell suspension. The term "intact sheet", as used herein, refers to a layer of cells which remain adherent to one another after the cells are harvested. The layer of cells can comprise one or more types of cells including RPE cells. Moreover, for use in transplantation, the population of retinal cells, e.g., neural retina cells or RPE cells, can comprise a relatively pure population of retinal cells. Preferred populations of retinal cells are, therefore, cell populations comprising preferably about 85% retinal cells, more preferably about 90% to 95%, about 98%, 99% retinal cells. The purity of a population of retinal cells can be determined by methods known in the art. For example, markers which specifically detect a particular retinal cell type, e.g., neural retina cells and/or RPE cells, can be used to detect the presence of the retina cell type and then the percentage of those cells in the population can be determined by visual observation. Examples of neural retina cell specific markers include, for example, neuron-specific enolase, interphotoreceptor retinoid-binding protein (IRBP), arrestin, and opsin. RPE specific markers include, for example, cytokeratin 8 and cytokeratin 18.

The modified or unmodified cells described herein can also be grown as a cell culture, i.e., as a population of cells which grow in vitro, in a medium suitable to support the growth of the cells. Media which can be used to support the growth of porcine retinal cells include mammalian culture media, such as those produced by Gibco BRL (Gaithersburg, Md.). The culture media can be, for example, low glucose Dulbecco's modified Eagle medium (DMEM). Other culture media suitable for the growth of retinal cells include Leibowitz L-15 (with bicarbonate) as described in Jensen et al. (1997) *Dev. Biol.* 188:267–279, the contents of which is incorporated herein by reference.

B. Retinal Cells Obtained at the Appropriate Age for Transplantation

For use in transplantation studies and treatment of retinal disorders, the retinal cells of the present invention are isolated at the appropriate stage of development in order to allow for growth, reproduction and differentiation following transplantation into an allogeneic or xenogeneic subject. Such retinal disorders include, for example, retinis pigmentosa, phototoxic retinopathy, light damaged retina, macular degeneration, gyrate atrophy, fundus flavimaculatus, Best's disease, Sorsby's dystrophy and Stargardt's disease in humans. Preferred retinal cells are, therefore, neural retinal cells, preferably porcine neural retina cells, more preferably fetal porcine neural retina cells, for use in treating retinis pigmentosa, phototoxic retinopathy, light damaged retina and macular degeneration; and RPE cells, preferably porcine RPE cells, more preferably fetal porcine RPE cells, for use in treating macular degeneration, gyrate atrophy, fundus flavimaculatus, Best's disease, Sorsby's dystrophy or Stargardt's disease. To provide for growth, reproduction and differentiation of porcine retinal cells, and in particular porcine neural retina cells and RPE cells, upon transplantation into a recipient subject, an optimal donor is selected. Typically, retinal cells of the invention are porcine fetal cells which are isolated from porcine fetuses. In one embodiment, the fetal porcine retinal cells are cultured in vitro until they display the desired characteristics for transplantation. For example, in general, RPE cells which are not sufficiently adherent to remain as an intact RPE sheet after harvest are too immature to harvest and transplant. Moreover, in general, neural retina cells which are too immature to harvest and transplant have characteristic morphology. The preferred morphology of RPE cells includes a rounded cell body which is essentially free, preferably free, of surrounding fibroblasts and which the cells are sufficiently adherent to each other such that an intact sheet of RPE cells can be obtained.

Thus, in one aspect of the invention, the porcine retinal cells can be obtained from a fetal pig at selected gestational ages. The retina consists of several layers including the RPE cell layer (which is the most external layer of the retina found in close conjunction with the choriod and choriocapillaris), the layer of rods and cones (i.e., the photoreceptor cells) and the bipolar and ganglionic cells. The RPE cell layer is thought to be a causative agent in the development of macular degeneration which accounts for the build up of metabolic by-products. This layer of cells does not readily replicate in adults, and therefore damage to the RPE layer can be irreversible and lead to the loss of photoreceptors and decreased visual acuity. Therefore, for treatment of retinal disorders, for example, disorders involving abnormal RPE cells, porcine RPE cells are isolated from the retina of a fetal donor swine (also referred to herein as "pig"). Preferably, RPE cells are isolated from a fetal pig at a selected gestational age. The selected gestational ages (the total gestation time for pig is 115 days) for isolation of cells was determined based on the following criteria: the ability to specifically dissect RPE cells essentially free, preferably free from fibroblasts, the ability to obtain intact sheets of RPE cells, and the viability of the RPE cells upon isolation. It was discovered that the preferred gestational age of fetal swine from which to obtain RPE cells suitable for transplantation into allogeneic and xenogeneic subjects, e.g., humans, is between about days sixty (60) to sixty-five (65). This preferred gestational age for porcine RPE cells was determined as described in Example I. The results of these experiments demonstrate that RPE cells obtained from swine younger than sixty days are not sufficiently adherent to obtain an intact RPE sheet. Moreover, in fetal swine younger than sixty days, the fibroblast are not as easily separated from the desired RPE cells. However, cells younger than sixty days can be used for transplantation if desired. In addition, the results of cell viability after isolation of cells from the fetuses of varying ages demonstrates that the number of viable RPE cells isolated decreases in fetuses older than about 70 days. Thus, the preferred range for isolation of porcine RPE cells is between about thirty (30) to one hundred (100) days of gestation, preferably about forty (40) to ninety (90) days of gestation. Another preferred range for isolation of porcine RPE cells is between about fifty (50) to eighty (80) days of gestation, preferably about sixty (60) to seventy (70) days of gestation. A particularly preferred age of fetal development for isolation of the porcine RPE cells of this invention is between sixty (60) to sixty-five (65) days of gestation.

The viability of RPE cells can be determined with esterase stain and the presence of proliferating RPE cells in vivo can be determined using Barr labeling as described, for example, in Jones et al. (1997) *Invest. Ophth. & Vis. Sci.* 38(4):1572. In addition, kits are commercially available which can be used to determine the viability of isolated RPE cells. For example, the LIVE/DEAD Viability/Cytotoxicity Kit, available from Molecular Probes (Eugene, Oreg.) can be used to determine the viability of the isolated RPE cell population.

In addition, the porcine retinal cells, e.g., RPE cells, can be grown as a cell culture until the cells demonstrate the preferred RPE morphology. For example, the RPE cells can be grown in vitro until the cells are sufficiently adherent to obtain an intact RPE sheet. Moreover, the purity of the RPE cells grown as a culture can be determined, for example, by detecting RPE specific markers in culture and then determining by visual observation the percentage of RPE cells in the population. RPE specific markers include, for example, cytokeratin 8 and cytokeratin 18. Such markers can be detected using marker specific antibodies. See, e.g., Nork et al. (1995) *Arch. Ophthalmol.* 113:791–802. Using such techniques, the purity of such a RPE cell population can, therefore, be determined. In preferred embodiments, the RPE cell population comprises at least about 85% to 90% RPE cells, preferably about 95%, 98%, 99% RPE cells.

C. An Isolated Population ofPorcine Retinal Cells

This invention also features an isolated population of cells obtained from porcine retina. For example, retinal cells can be obtained from the ocular globe by hemisecting the globe at the ora serrata and the anterior segment. The neural retina can be separated from surrounding retinal tissue and a population of neural retina cells can be isolated. In addition, the eye cup can be isolated from the porcine retina and RPE cells can be separated from the sclera to obtain a population of RPE cells. As used herein, the term "isolated" refers to a cell or population of cells which has been separated from its natural environment, e.g., removal from the donor animal, e.g., pig, and alteration of the cell's relationship with neighboring cells in which it is contact. The isolated cell or population of cells can be in the form of a tissue sample, e.g., an intact sheet of cells, e.g., a monolayer of RPE cells, or it can be in a cell suspension. When used to refer to a population of porcine retinal cells, e.g., neural retina cells and/or RPE cells, the term also includes populations of cells which result from the proliferation of the isolated cells of the invention. The term "population" is intended to include two or more cells. Cells in a population can be obtained from the same or different source(s), e.g., the same swine or several different swine.

In one aspect of the invention, the population of cells is a substantially pure population of retinal cells. The term "substantially pure" as used herein refers to a population of retinal cells comprising at least about 85% to 90% retinal cells, preferably about 95%, 98%, 99% retinal cells. The purity of a retinal cell population, e.g., RPE cell or neural retinal cell population, grown as a culture can be determined, for example, by detecting markers specific for various cell types in culture and then determining by visual observation the percentage of cell types in the population. For example, neural retinal cells can be detected based on the presence of neural cell specific markers such as interphotoreceptor retinoid-binding protein (IRBP), arrestin, and opsin. In addition, RPE cells can be detected based on the presence of RPE specific markers such as cytokeratin 8 and cytokeratin 18. Such markers can be detected using marker specific antibodies. See, e.g., Nork et al. (1995) *Arch. Ophthalmol.* 113:791–802. Using such techniques, the purity of a retinal cell population can be determined.

Cells obtained from porcine retina can include neural retina cells, RPE cells, iris epithelial cells and/or progenitor cells thereof. Progenitor or precursor cells can be distinguished from committed cells by, for example, differential staining. For example, immature neuroepithelial cells (e.g., neural retinal progenitor cells) express nestin and can be identified with a nestin-specific stain while mature retinal cells such as neural retina cells generally do not express nestin. In addition, mature retinal cells, e.g., neural retina cells, express neuron-specific enolase and can be identified by enolase-specific stain while immature retinal cells, e.g., neuroepithelial cells, generally do not express neuron-specific enolase.

D. Retinal Cells Isolated From Essentially Pathogen-Free Swine

In another embodiment, the retinal cells of the invention are cells determined to be free from at least one organism which originates in the animal from which the cells are obtained and which transmits infection or disease to a recipient subject. Preferably the cell is determined to be free from at least two organisms. Retinal cells with these characteristics can be obtained by screening the animal to determine if it is essentially free from organisms or substances which are capable of transmitting infection or disease to a xenogeneic recipient, e.g., a human recipient, of the cells. Typically, the cells are porcine cells which are obtained from a swine which predetermined to be essentially free from pathogens which detrimentally affect humans. For example, the pathogens from which the swine are free include, but are not limited to, one or more of pathogens from the following categories of pathogens: zoonotic, cross-placental, neurotropic and ocular-infecting. As used herein, "zoonotic" refers to organisms which can be transferred from pigs to man under natural conditions; "cross-placental" refers to organisms capable of crossing the placenta from mother to fetus; "neurotropic" refers to organisms which selectively infect neural cells; and "ocular-infecting" refers to organisms which selectively infect cells of the eye. Within each of these categories, the organism can be a parasite, bacterium, mycoplasma, and/or virus. For example, the swine can be free from parasites such as zoonotic parasites (e.g., toxoplasma), cross-placental parasites (e.g., eperythozoon suis or toxoplasma), neurotropic parasites (e.g., toxoplasma), ocular-infecting parasites, and/or mycoplasma, such as M. hypopneumonia. Additionally, the swine can be free from bacteria such as zoonotic bacteria (e.g., brucella, listeria, mycobacterium TB, leptospirillum), cross-placental bacteria (e.g., brucella, listeria, leptospirillum), neurotropic bacteria (e.g., listeria), and/or ocular-infecting bacteria. Specific examples of bacteria from which the swine can be free include brucella, clostridium, hemophilus suis, listeria, mycobacterium TB, leptospirillum, salmonella and hemophilus suis. Additionally, the swine can be free from viruses such as zoonotic viruses, viruses that can cross the placenta in pregnant sows, neurotropic viruses, and ocular-infecting viruses. Zoonotic viruses include, for example, a virus in the rabies virus group, a herpes-like virus which causes pseudorabies, encephalomyocarditis virus, swine influenza Type A, transmissible gastroenteritus virus, parainfluenza virus 3 and vesicular stomatitis virus. Cross-placental viruses include, for example, viruses that cause porcine respiratory reproductive syndrome, a virus in the rabies virus group, a herpes-like virus which causes pseudorabies, parvovirus, a virus that causes swine vesicular disease, teschen (porcine polio virus), hemmaglutinating encephalomyocarditis, cytomegalovirus, suipoxvirus, and swine influenza type A. Neurotropic viruses include, for example, a virus in the rabies virus group, a herpes-like virus which causes pseudorabies, parvovirus, encephalomyocarditis virus, a virus which causes swine vesicular disease, porcine poliovirus (teschen), a virus which causes hemmaglutinating encephalomyocarditis, adenovirus, parainfluenza 3 virus. Specific examples of viruses from which the swine are free include: a virus which causes (or results in) porcine respiratory reproductive syndrome, a virus in the rabies virus group, a herpes-like virus which causes pseudorabies, parvovirus, encephalomyocarditis virus, a virus which causes swine vesicular disease, porcine poliovirus (teschen), a virus which causes hemmaglutinating encephalomyocarditis, cytomegalovirus, suipoxvirus, swine influenza type A, adenovirus, transmissible gastroenteritus virus, a virus which causes bovine viral diarrhea, parainfluenza virus 3, and vesicular stomatitis virus.

In one embodiment, the pigs from which the retinal cells are isolated are essentially free from the following organisms: Toxoplasma, eperythrozoon, brucella, listeria, mycobacterium TB, leptospirillum, hemophilus suis, M. Hypopneumonia, a virus which causes porcine respiratory reproductive syndrome, a virus which causes rabies, a virus which causes pseudorabies, parvovirus, encephalomyocarditis virus, a virus which causes swine vesicular disease, porcine polio virus (teschen), a virus which causes hemagglutinating encephalomyocarditis, suipoxvirus, swine influenza type A, adenovirus, transmissible gastroenteritis virus, a virus which causes bovine viral diarrhea, and vesicular stomatitis virus. The phrase "essentially free or free from organisms or substances which are capable of transmitting infection or disease to a xenogeneic recipient" (also referred to herein as "essentially pathogen-free" or "pathogen free") when referring to a swine from which cells are isolated or to the cells themselves means that swine does not contain organisms or substances in an amount which transmits infection or disease to a xenogeneic recipient, e.g. a human. Example III provides representative, but not limiting, examples of methods for selecting swine which are essentially free from various organisms. The cells of the invention can be isolated from fetal or post-natal swine which are determined to be essentially free of such organisms. These swine are maintained under suitable conditions until used as a source of cells for transplantation.

Preferred retinal cells isolated from the essentially pathogen free swine include neural retina cells, RPE cells and iris epithelial cells. Optimal gestational ages of the swine from which these cells are isolated are described in detail herein. Porcine retinal cells isolated from essentially pathogen-free swine can additionally be modified to reduce the immunogenecity of the cells upon transplantation into a xenogeneic subject as described herein.

II. Methods of the Invention

A. Method for Isolating Porcine Retinal Cells from an Essentially Pathogen-Free Swine Another aspect of the invention pertains to a method for isolating a porcine retinal cell, e.g., a neural retina cell, a RPE cell or a iris epithelial cell, from a pig predetermined to be free from at least two organisms which originate in pig and which are capable of transmitting infection or disease to a xenogeneic recipient of the cells. According to the method, swine are tested for the presence or absence of organisms which are capable of transmitting infection or disease to a xenogeneic recipient, e.g., a human recipient, of the cells. Such pathogens from which the swine are free include, but are not limited to, one or more of pathogens from the following categories of pathogens: zoonotic, cross-placental, neurotropic, and ocular-infecting. Within each of these categories, the organism can be a parasite, bacterium, mycoplasma, and/or virus. The swine can be free from, for example, zoonotic, cross-placental, neurotropic, and/or ocular-infecting parasites or mycoplasma (e.g., M. hypopneumronia). Specific examples of parasites from which the swine are free include: toxoplasma and eperylherozoon. The swine can further be free from, for example, zoonotic, cross-placental, neurotropic, and/or ocular-infecting bacteria. Examples of bacteria from which the swine can be free include brucella, listeria, mycobacterium TB, leptospirillum, and hemophilus suis. Additionally, the swine can be free from viruses such as zoonotic, cross placenta, neurotropic, and/or ocular-infecting viruses. Specific examples of viruses from which the swine are free include: a virus which causes (or results in) porcine respiratory reproductive syndrome, a virus in the rabies virus group, a herpes-like virus which causes pseudorabies, parvovirus, encephalomyocarditis virus, a virus which causes swine vesicular disease, porcine poliovirus (teschen), a virus which causes hemmaglutinating encephalomyocarditis, cytomegalovirus, suipoxvirus, swine influenza type A, adenovirus, transmissible gastroenteritis virus, a virus which causes bovine viral diarrhea, parainfluenza virus 3, and vesicular stomatitis virus. Preferably, retinal cells are isolated from embryos of swine which are predetermined to be essentially free of these organisms.

Methods for isolating retinal cell tissue are known in the art and described herein. For example, RPE sheets can be dissected from eye cups or sheets containing a RPE cell layer and choroid tissue can be obtained, e.g., by dissecting the tissue under a microscope. The RPE cells in the retinal tissue can then be dissociated by chemical means, e.g., enzymes, or by mechanical means, e.g., chopping and/or successive pipette trituration. In addition, neural retina cells can be dissected away from the eye cup and then can be dissociated by chemical means or mechanical means. The swine which are employed in the method of the invention as a source of retinal cells include fetal swine (swine fetuses) and postnatal swine. If a fetal swine is to be used as a source of retinal cells, semen from a boar which has been tested to be essentially free of disease transmitting organisms is employed to artificially inseminate a female swine which is essentially free from such organisms. At a selected gestational age, e.g., the gestational age of a retinal cell type, e.g., a RPE cell, described herein, a hysterectomy is performed under appropriate conditions of sterility and the fetuses are thereafter removed in their individual amniotic sacs. Appropriate retinal cells or tissue are thereafter recovered under appropriate conditions of sterility.

The swine determined to be essentially free from organisms which originate in pigs and which transmit infection or disease to a recipient subject can be employed as a source of a wide variety of cells, e.g., retinal cells. Porcine retinal cells which can be isolated according to this method include, for example, RPE cells and neural retina cells as described in further detail herein. Porcine retinal cells isolated from essentially pathogen-free swine can additionally be modified as described herein.

B. Method for Treating Retinal Disorders of an Allogeneic or Xenogeneic Subject Using Modified Retinal Cells A still further aspect of the invention pertains to methods for treating retinal disorders in an allogeneic or xenogeneic subject, particularly a human subject, in which retinal cells, e.g., porcine retinal cells, are introduced into the retina, e.g., subretinal space, of the subject. As used herein, the phrase "retinal disorders" includes an impairment or absence of a normal retinal cell function and/or presence of an abnormal retinal cell function. For example, an impairment or presence of an abnormal retinal function can result in loss or reduction of visual acuity. The retinal cells, in unmodified form, have at least one antigen on the cell surface which is capable of stimulating an immune response against the cell in a xenogeneic subject. Prior to transplantation, the antigen on the cell surface is altered to inhibit rejection of the cell when introduced into the xenogeneic subject. As used herein, the term "introducing" is used interchangeably with the term "transplanting". The retinal cells of the invention are introduced into a subject by any appropriate route which results in delivery of the cells to a desired location in the subject. For example, one method of administration of cells into the subretinal space of a subject is by direct injection of the cells using the transvitreal approach. See e.g., Sheng et al. (1990) *Invest. Ophthal. & Vis. Sci.* 36:381–390; Gouras et al. (1991) *Invest. Ophthal. & Vis. Sci.* 35:3145–3153. Cells can be administered in a pharmaceutically acceptable carrier, such as a buffered saline solution. Another method which can be used to administer sheets of RPE cells to the subretinal space of a subject is to fold the RPE layer into a specially designed pipette with a tapered gauge for delivery into the subretinal space. The pipette is inserted through a retinotomy and the RPE layer is injected as described in further detail in PCT publication WO 96/26759, published on Sep. 6, 1996, the contents of which are incorporated herein by reference. An "RPE layer" as used herein refers to a RPE cell monolayer. Cells which are the be administered as a monolayer, can be stabilized in support matrix such as gelatin as described herein and in PCT publication WO 91/02499, published Mar. 7, 1991, the contents of which are incorporated herein by reference. In addition, other substrates which can be used to stabilize the monolayer include lectins such as concanavalin A and wheat germ agglutin. The number of retinal cells used to treat retinal disorders in a subject depends on the size of the lesion. For example, to treat retinal disorders in a human subject, about $10^5$ to $10^6$ retinal cells of the invention are introduced into the retina, e.g., subretinal space, of the human subject.

The retinal cells of the invention can be inserted into a delivery device which facilitates introduction by e.g., injection, of the cells into the subjects. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The retinal cells of the invention can be inserted into such a delivery device, e.g., a syringe, in the form of a solution. Alternatively, the cells can be embedded in a support matrix when contained in such a delivery device. In another embodiment, the cells can be introduced as a monolayer into the subject by harvesting and inserting the cells, as a monolayer, using a pipette with a tapered gauge tip as described in PCT publication WO 96/26759. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by using a pharmaceutically acceptable carrier or diluent and, as required, other ingredients enumerated above, followed by filtered sterilization, and then incorporating porcine retinal cells as described herein.

Support matrices in which the retinal cells can be incorporated or embedded include matrices which are recipient-compatible and which degrade into products which are not harmful to the recipient. Natural and/or synthetic biodegradable matrices are examples of such matrices. Natural biodegradable matrices include gelatin and collagen matrices. Synthetic biodegradable matrices include synthetic polymers such as polyanhydrides, polyorthoesters, and polylactic acid. In a preferred embodiment, the support matrix is gelatin.

The methods of the invention are particularly useful for treating human subjects with retinal disorders. Such retinal disorders can be the result of disease, injury, genetics and/or aging. As used herein, retinal disorders include morphological and/or functional abnormality of a retinal cell or a population of retinal cells. Non-limiting examples of morphological and functional abnormalities of retinal cells include physical deterioration and/or death of retinal cells, abnormal growth patterns of retinal cells or the surrounding vasculature, abnormalities in the physical connection between retinal cells with each other or underlying tissue layers (e.g., Bruch's membrane or choroid tissue), failure of retinal cells such as RPE cells to function as they normally function (e.g., to phagocytize and digest metabolic debris), failure of retinal cells such as neural retinal cells to produce a substance which it normally produces (e.g., rhodopsin or iodopsin) and/or failure of retinal cells such as neural retina cells to initiate visual stimulus. Morphological and/or functional abnormalities of retinal cells are seen with many disorders including, for example, retinis pigmentosa, phototoxic retinopathy, light damaged retina, Sorsby's dystrophy, Stargardt's disease and macular degeneration.

In one embodiment of the invention, porcine retinal cells are obtained from fetal pigs. For example, porcine RPE cells preferably obtained from fetal porcine retina at about days sixty (60) to seventy (70) of gestation, are transplanted into the retina, e.g., subretinal space, of a human subject to treat a retinal disorder such as macular degeneration.

Transplantation of retinal cells of the invention into the retina of a human subject having a retinal disorder can result in improved visual acuity and/or reduction of further loss of visual acuity. The term "subject" is intended to include mammals, particularly humans, susceptible to injury-, age-, and/or disease-related retinal disorders. The term "subject" also includes mammals. Examples of subjects include primates (e.g., humans, and monkeys). A "xenogeneic subject" as used herein is a subject into which cells of another species are transplanted or are to be transplanted. Porcine retinal cells are introduced into a subject in an amount suitable to at least reduce or decrease further loss of visual acuity and/or partially correct loss of visual acuity caused by a retinal disorder. Preferred porcine retinal cells are RPE cells and neural retina cells obtained from fetal swine and at selected fetal ages described in detail herein.

Prior to introduction into a subject, the retinal cells can be modified to inhibit immunological rejection. The retinal cells can, as described in detail above, be rendered suitable for introduction into an allogeneic or xenogeneic subject by alteration of at least one immunogenic cell surface antigen (e.g., an MHC class I antigen). To inhibit rejection of transplanted retinal cells and to achieve immunological non-responsiveness in an allogeneic or xenogeneic transplant recipient, the method of the invention can include alteration of immunogenic antigens on the surface of the retinal cells prior to introduction into the subject. This step of altering one or more immunogenic antigens on retinal cells can be performed alone or in combination with administering to the subject of an agent which inhibits T cell activity in the subject. Alternatively, inhibition of rejection of a retinal cell graft can be accomplished by administering to the subject an agent which inhibits T cell activity in the subject in the absence of prior alteration of an immunogenic antigen on the surface of the retinal cell. As used herein, an agent which inhibits T cell activity is defined as an agent which results in removal (e.g., sequestration) or destruction of T cells within a subject or inhibits T cell functions within the subject (i.e., T cells may still be present in the subject but are in a non-ftnctional state, such that they are unable to proliferate or elicit or perform effector functions, e.g. cytokine production, cytotoxicity etc.). The term "T cell" encompasses mature peripheral blood T lymphocytes. The agent which inhibits T cell activity may also inhibit the activity or maturation of immature T cells (e.g., thymocytes).

A preferred agent for use in inhibiting T cell activity in a recipient subject is an immunosuppressive drug. The term "immunosuppressive drug or agent" is intended to include pharmaceutical agents which inhibit or interfere with normal immune function. A preferred immunsuppressive drug is cyclosporin A. Other immunosuppressive drugs which can be used include FK506, and RS-61443. In one embodiment, the immunosuppressive drug is administered in conjunction with at least one other therapeutic agent. Additional therapeutic agents which can be administered include steroids (e.g., glucocorticoids such as prednisone, methyl prednisolone and dexamethasone) and chemotherapeutic agents (e.g., azathioprine and cyclosphphamide). In another embodiment, an immunosuppressive drug is administered in conjunction with both a steroid and a chemotherapeutic agent. Suitable immunosuppressive drugs are commercially available (e.g., cyclosporin A is available from Novartis, Corp., East Hanover, N.J.).

An immumsuppressive drug is administered in a formulation which is compatible with the route of administration. Suitable routes of administration include intravenous injection (either as a single infusion, multiple infusions or as an intravenous drip over time), intraperitoneal injection, intramuscular injection and oral administration. For intravenous injection, the drug can be dissolved in a physiologically acceptable carrier or diluent (e.g., a buffered saline solution) which is sterile and allows for syringability. Dispersions of drugs can also be prepared in glycerol, liquid polyethylene glycols, and mixtures thereof and in oils. Convenient routes of administration and carriers for immunsuppressive drugs are known in the art. For example, cyclosporin A can be administered intravenously in a saline solution, or orally, intraperitoneally or intramuscularly in olive oil or other suitable carrier or diluent.

An immunosuppressive drug is administered to a recipient subject at a dosage sufficient to achieve the desired therapeutic effect (e.g., inhibition of rejection of transplanted cells). Dosage ranges for immunosuppressive drugs, and other agents which can be coadministered therewith (e.g., steroids and chemotherapeutic agents), are known in the art (See e.g., Freed et al. *New Engl. J. Med.* (1992) 327:1549: Spencer et al. (1992) *New Engl. J. Med.* 327:1541; Widner et al. (1992) *New Engl. J. Med.* 327:1556; Lindvall et al. (1992) *Ann. Neurol.* 31:155; and Lindvall et al. (1992) *Arch. Neurol.* 46:615). A preferred dosage range for immunosuppressive drugs, suitable for treatment of humans, is about 1–30 mg/kg of body weight per day. A preferred dosage range for cyclosporin A is about 1–10 mg/kg of body weight per day, more preferably about 1–5 mg/kg of body weight per day. Dosages can be adjusted to maintain an optimal level of the immunosuppressive drug in the serum of the recipient subject. For example, dosages can be adjusted to maintain a preferred serum level for cyclosporin A in a human subject of about 100–200 ng/ml. It is to be noted that dosage values may vary according to factors such as the disease state, age, sex, and weight of the individual. Dosage regimens may be adjusted over time to provide the optimum therapeutic response according to the individual need and the professional judgment of the person administering or supervising the administration of the compositions, and that the dosage ranges set forth herein are exemplary only and are not intended to limit the scope or practice of the claimed composition.

In one embodiment of the invention, an immunsuppressive drug is administered to a subject transiently for a sufficient time to induce tolerance to the transplanted cells in the subject. Transient administration of an immunosuppressive drug has been found to induce long-term graft-specific tolerance in a graft recipient (See Brunson et al. (1991) *Transplantation* 52:545; Hutchinson et al. (1981) *Transplantation* 32:210; Green et al. (1979) *Lancet* 2:123; Hall et al. (1985) *J. Exp. Med.* 162:1683). Administration of the drug to the subject can begin prior to transplantation of the cells into the subject. For example, initiation of drug administration can be a few days (e.g., one to three days) before transplantation. Alternatively, drug administration can begin the day of transplantation or a few days (generally not more than three days) after transplantation. Administration of the drug is continued for sufficient time to induce donor cell-specific tolerance in the recipient such that donor cells will continue to be accepted by the recipient when drug administration ceases. For example, the drug can be administered for as short as three days or as long as three months following transplantation. Typically, the drug is administered for at least one week but not more than one month following transplantation. Induction of tolerance to the transplanted cells in a subject is indicated by the continued acceptance of the transplanted cells after administration of the immunosuppressive drug has ceased. Acceptance of transplanted tissue can be determined morphologically (e.g., with skin grafts by examining the transplanted tissue or by biopsy) or by assessment of the functional activity of the graft.

Another type of agent which can be used to inhibit T cell activity in a subject is an antibody, or fragment or derivative thereof, which depletes or sequesters T cells in a recipient. Antibodies which are capable of depleting or sequestering T cells in vivo when administered to a subject are known in the art. Typically, these antibodies bind to an antigen on the surface of a T cell. Polyclonal antisera can be used, for example anti-lymphocyte serum. Alternatively, one or more monoclonal antibodies can be used. Preferred T cell-depleting antibodies include monoclonal antibodies which bind to CD2, CD3, CD4 or CD8 on the surface of T cells. Antibodies which bind to these antigens are known in the art and are commercially available (e.g., from American Type Culture Collection). A preferred monoclonal antibody for binding to CD3 on human T cells is OKT3 (ATCC CRL 8001). The binding of an antibody to surface antigens on a T cell can facilitate sequestration of T cells in a subject and/or destruction of T cells in a subject by endogenous mechanisms. Alternatively, a T cell-depleting antibody which binds to an antigen on a T cell surface can be conjugated to a toxin (e.g., ricin) or other cytotoxic molecule (e.g., a radioactive isotope) to facilitate destruction of T cells upon binding of the antibody to the T cells. See U.S. patent application Ser. No.: 08/220,724, filed Mar. 31, 1994, for further details concerning the generation of antibodies which can be used in the present invention.

Another type of antibody which can be used to inhibit T cell activity in a recipient subject is an antibody which inhibits T cell proliferation. For example, an antibody directed against a T cell growth factor, such as IL-2, or a T cell growth factor receptor, such as the IL-2 receptor, can inhibit proliferation of T cells (See e.g., DeSilva, D. R. et al. (1991) *J. Immunol.* 147:3261–3267). Accordingly, an IL-2 or an IL-2 receptor antibody can be administered to a recipient to inhibit rejection of a transplanted cell (see e.g. Wood et al. (1992) *Neuroscience* 49:410). Additionally, both an IL-2 and an IL-2 receptor antibody can be coadministered to inhibit T cell activity or can be administered with another antibody (e.g., which binds to a surface antigen on T cells).

An antibody which depletes, sequesters or inhibits T cells within a recipient can be administered at a dose and for an appropriate time to inhibit rejection of cells upon transplantation. Antibodies are preferably administered intravenously in a pharmaceutically acceptable carrier or diluent (e.g., a sterile saline solution). Antibody administration can begin prior to transplantation (e.g., one to five days prior to transplantation) and can continue on a daily basis after transplantation to achieve the desired effect (e.g., up to fourteen days after transplantation). A preferred dosage range for administration of an antibody to a human subject is about 0.1–0.3 mg/kg of body weight per day. Alternatively, a single high dose of antibody (e.g., a bolus at a dosage of about 10 mg/kg of body weight) can be administered to a human subject on the day of transplantation. The effectiveness of antibody treatment in depleting T cells from the peripheral blood can be determined by comparing T cell counts in blood samples taken from the subject before and after antibody treatment. Dosage regimes may be adjusted over time to provide the optimum therapeutic response according to the individual need and the professional judgment of the person administering or supervising the administration of the compositions. Dosage ranges set forth herein are exemplary only and are not intended to limit the scope or practice of the claimed composition.

The present invention is further illustrated by the following examples which in no way should be constried as being fuirther limiting. The contents of all cited references cited throughout this application are hereby expressly incorporated by reference.

EXAMPLES

Example I.

Methods of Isolating Porcine RPE Cells

RPE cells were obtained from porcine fetal eyes under different conditions to allow testing of four preparations for transplantation. These conditions were: (1) suspensions of freshly isolated RPE cells, (2) sheets of freshly isolated RPE embedded in gelatin prior to transplantation, (3) RPE cells cultured and trypsinized to inject as a suspension, and (4) RPE cells cultured and lifted from the culture dish as a monolayer prior to embedding in gelatin and transplantation.

Pregnant pigs (with a normal gestational period of 115 days) were obtained from Tufts Veterinary School (Grafton, Mass.) and fetuses were used for isolation of the RPE cells for transplantation. The pregnant pigs were obtained at gestational ages of approximately 40 to 80 days. The animals were exsanguinated following standard veterinary procedures, the uterus removed and tranfered to sterile phosphate buffered saline (PBS). Under a laminar flow hood, the larger fetuses had their eyes removed and transferred to Dulbecco's PBS (DPBS) with 50 μg/ml gentamicin at 4° C. Smaller fetuses were placed into DPBS with gentamicin at 4° C. until the eyes could be removed. Male fetuses were identified and selected as donors for retinas in experiments involving detection using the Y chromosome probe as describe in detail below.

Isolation of the RPE

The eyes were placed in a horizontal flow hood with a dissecting microscope and prepared for overnight digestion in one of three ways:

1) The eyes were digested whole by removing only the tissue down to the corneal epithelium. The eyes were placed in a 50 ml tube with 2 ml of the neutral metalloproteinase, Dispase (Dispase II, Boehringer Mannheim) in DPBS per eye, using ice cold 0.5% to 2% Dispase. The eyes were placed in tubes on ice overnight.

2) "Eye cups" were also prepared for digestion by placing the eye in a petri dish with ice cold DPBS. The exterior of the eye was cleaned of residual tissue and a cut was made into the sclera posterior to the neural retina and from the optic nerve to the developing iris using fine scissors. The cut was extended circumferentially to remove the cornea and lens by making three similar cuts with a scalpel to effectively quarter the eye. The vitreous humor was removed from the interior of the eye, and much of the neural retina was removed with the vitreous humor. Scissors and forceps were used to remove as much of the remaining retina as possible without damaging the pigmented epithelium. Eye cups were then digested in the same enzyme preparations as the whole eyes.

3) "RPE/choroid sheets" were prepared by removing the eye cup and separating the sclera and RPE/choroid. 2 mm squares were produced on each side of RPE with attached horoid from the eye cup by making rocking cuts with the scalpel, removing as much emaining retina as possible without damaging the pigmented epithelium. The RPE/schlera quares were stored in DPBS at 4° C. for at least 12 hours prior to Dispase digestion. The Dispase solution (12.5 U/ml Dispase) was refiltered immediately prior to digestion using a 0.2 μm pore size. The squares were transferred with large bore 5 ml pipettes into a digestion solution (1 eye/1 ml in 15 ml tubes) while minimizing dilution of Dispase by allowing the pieces to settle in the mouth of the pipette. The tissue was digested for 8 to 12 hours on ice in the Dispase soltion.

Eye cups and RPE/choroid sheets were transferred in cold Dispase to a shallow petri dish containing 20 ml cold DPBS under a dissecting microscope within a horizontal flow tissue culture hood to obtain RPE sheets. The edge of the RPE/choroid layer had begun to separate from the underlying tissue as visualized by the presence of visible blood vessels in the choroid. The schlera and choroid were grasped with fine forceps and using a plugged Pasteur pipette the RPE layer was gently blown away from the choroid. Care was taken to avoid cytolytic bubbles. By working along the interface, the RPE sheet was gently pealed away. The RPE sheet was rinsed in DPBS. The RPE sheet was then mounted in 50% gelatin with 300 mM sucrose in $CO_2$-independent medium by melting gelatin at 37° C. for 4 minutes and transferring to 4° C. for 4 minutes. The mounted RPE sheets were stored at 4° C. in $CO_2$-independent medium.

The comparison of whole eyes, eyecups, and RPE/choroid sheets revealed that the eye cups and RPE/choroid sheets were preferable preparations for the enzymatic release of the RPE layer from the retina. With both these preparations, RPE sheets free from contaminating choriocapillaris and neural retina were obtained. Enzymatic digestion of the cells from Bruch's membrane was very effective using RPE/choroid sheets.

Cell Cultures

The RPE sheet was transferred by pipetting into a large bore pipette tip. After rinsing in PBS the cells were preplated to remove contaminating cells (fibroblasts) by transferring sheets to culture medium (DMEM with 10% heat inactivated fetal calf serum (FCS) containing 2 mM L-glutamine (BioWhittaker) and 50 μg/ml gentamicin (BioWhittaker) in a 60 mm tissue culture dish. Cells were allowed to settle for at least 20 minutes, while watching that the RPE sheet did not adhere to the dish. The RPE sheet was transferred to a 12-well tissue culture plate previously coated with 0.1 μg/ml poly-L-lysine (150–300 kD molecular weight) in sterile water for 0.5 hour at room temperature. The RPE sheet was placed into the culture well containing 0.5 ml medium and flattened gently with the forceps. After allowing the sheet to adhere to the coated plastic surface, cells began to grow out from the tissue within 24 hours. These cells were harvested with 0.05% trypsin with 0.02% EDTA.

Under these conditions, the RPE cells remain as a heavily pigmented monolayer. In some of the cultures, the RPE monolayer was stabilized in a thin sheet by pouring 4% gelatin at 41° C. into the dish. Small 2 or 3mm round buttons were punched from the dishes after cooling to 37° C. and delivered into the subretinal space as described below. Alternatively, some of the cultures were used to prepare RPE cell suspensions. The RPE cells were trypsinized and the cell suspension used for injection into the subretinal space. If the RPE cells do not readily dissociate from the attached choroid, the RPE layer was cultured by placing this tissue, cells down, onto a poly-L-lysine coated tissue culture plate. The excess tissue was removed after the RPE cells attached.

Using these various isolation conditions, several different gestational ages for isolation of RPE sheets were examined. Dissociated cells were obtained from animals of gestational ages of 44, 56 and 77 days of a total of 115 days of pig gestation.

These studies indicated that overnight digestion of whole fetal eyes most reliably generates cultures. In addition, overnight treatment of RPE/choroid sheets resulted in RPE sheets with 0.5%–1% Dispase. It was also found that the later gestational ages (e.g., between about days 63 and 71 of gestation) used were optimal for obtaining intact sheets of RPE for transplantation. Pure cultures of RPE cells were obtained from eyes of day 44, 56, 63 and 71 fetuses. Fibroblasts were observed in some cultures, but by using the preplating protocol described above, RPE cultures free of other cells types were obtained. In fetuses removed at day 38 of gestation and early, the fetal eyes are at a lower size limit. In addition, before 56 days the RPE layer is not sufficiently adherent to obtain an intact sheet and it was demonstrated that day 63 fetal eyes gave sheets after overnight digestion with the greatest integrity.

Determining Viability of Isolated RPE cells

The porcine RPE cells are tested for their phagocytic capacity by adding human photoreceptor outer segments to the cultured cells as described in Gouras et al.(1994) *Graefe's Arch. Clin. Exp. Ophthamol*. 232:599–607. Viable RPE cells should take up and digest the exogenous outer segments.

Example II.

Transplatation of Porcine RPE Cells

Porcine donor RPE cells are transplanted onto Bruch's membrane in the host animal after debridement of native RPE in the host animal. The purpose of this experiment is to demonstrate that the transplanted RPE are capable of preventing atrophy of the subfoveal choriocapillaris and to determine whether transplantation of fetal RPE cells 24 hours after RPE debridement with miromycin prevents secondary atrophy of the choriocapillaris and damage to the overlying retina. In order to definitively identify transplanted cells, a porcine Y chromosome probe is used in transplants of RPE cells into female porcine recipients.

Generation of a Y Chromosome Probe

Repetitive sequences on the pig Y chromosome were identified by searching sequence databases or by a subtractive hybridization procedure in which female genomic DNA was used to remove shared sequences from male DNA. Repetitive sequences are preferred because male specific genes that could be used for identification are only expressed at specific developmental stages and are not reliable markers for the cells as they mature. Repetitive sequences provide amplification of the signal as shown previously with porcine specific repetitive sequences that was used for graft identification in another cellular transplant model. See Oettinger et al. (1995) *Cell Transplant*. 4:253–256. The repetitive sequences was amplified by polymerase chain reaction (PCR), cloned into pGEM7zf, and labeled by PCR with digoxygenin dUTP.

Use of Y Chromosome Probe for in Situ Hybridization

The probe is used for in situ hybridization on paraffin or plastic embedded sections. Conditions for tissue digestion with proteinase K and for hybridization in formamide are defined for the porcine retina by previously established protocols. See Oettinger et al. (1995) Cell Transplant. 4:253–256. Final detection of the digoxygenin labeled probe was accomplished using HRP-labeled anti-digoxygenin antibody, and horseradish peroxidase with nitro blue tetrazolium chloride and 5-bromo-4-chloro-e-indolyl-phosphate (NBT/BCIP) staining.

The nucleotide sequence of a Y chromosome probe was obtained and labeling of the insert with digoxygenin by PCR was successful and allowed us to generate a probe to test on histological sections of male and female tissues. This probe reacted by in situ hybridization with the nuclei of male but not with female porcine cell. This probe is, therefore, an important tool for use in the RPE transplantation studies in which fetal porcine cells from male fetuses will be transplanted into female pigs. In addition to the histological studies performed to evaluate preservation of choriocapillaris and neural retina this probe allows the discrimination between host and donor RPE cells to be accomplished without leaving identification open to question.

Generation of an Animal Model of Macular Degeneration

Surgical preparation of eye for RPE debridement

A standard 3-port pars plana vitrectomy is performed using instruments and surgical techniques which are currently being used for vitreous surgery in the human. The conjunctiva is opened for vitrectomy incisions, and a self-retaining infusion cannula is placed through the pars plana in one of the inferior quadrants. Sclerotomes are then made through the pars plana in the two superior quadrants for the surgical instruments. A light pipe is introduced into the vitreous cavity through the left-hand instrument port, and a microvitrector is introduced through the right hand instrument port. A core pars plana vitrectomy is then performed. The sheet of cortical vitreous which remains adherent to the underlying retina in these young animals can be identified by applying suction over the retinal surface with a soft-tip silicone catheter. After this sheet of cortical vitreous is identified, it is surgically excised with the vitrectomy instruments.

After the completion of the pars plana vitrectomy, a microinjector with fine foot pedal control and a 25 gauge blunt tip is used to inject saline containing the calcium chelating agent EDTA and $10^{-3}$ mg/ml of mitomycin-C into the subretinal space for 20 minutes.

RPE debridement

The calcium chelating agent EDTA loosens the attachment between RPE cells and native Bruch's membrane. Loosely adherent RPE can then be removed by entering the subretinal space with a sort-tip fluted silicon cannula (Dutch Ophthalmic Research Corporation) and brushing Bruch's membrane with the soft-tipped silicone catheter. Fluid is aspirated from the subretinal space together with loosened RPE cells, and the subretinal space is irrigated with 0.125% EDTA to remove residual mitomycin and residual loose, dissociated RPE. Any RPE cells circulating free in the vitreous cavity is then removed, and a fluid-gas exchange is performed to facilitate complete removal of the cells.

Fluorescein angiography after RPE debridement

After the induction of anesthesia using standard veterinary procedures, the animal's pupil is dilated with 2 drops of 1% mydriacyl and 2.5% phenylephrine. A fluorescein camera with excitation and emission filters matched to the excitation and emission wavelengths of fluorescein is used. Intravenous access is established, and 5cc of sodium fluorescein (10%) is injected intravenously. Fundus photographs are taken with T-max 400 black and white film immediately before fluorescein injection and in rapid sequence after fluorescein injection; late photos are taken 10 minutes after injection.

Transplantation of RPE into Animal Model of Macular Degeneration

Transplantation of RPE into the debrided animal model

Male and female domestic pigs less than 6 months of age are used. Animals are sedated with 0.01 mg/kg of buprenorphine hydrochloride intramuscularly (IM) immediately after surgery and 12 hours later. Animals are maintained for up to 3 months after surgery.

The RPE cells are transplanted into the subretinal space one day after RPE debridement. Fetal RPE cells are prepared for transplantation in each of four conditions described in Example I:

a. fetal porcine RPE in sheets
b. dissociated fetal porcine RPE
c. cultured fetal porcine RPE in sheets
d. dissociated cultured fetal porcine RPE Twenty-four hours after debridement, RPE cells are transplanted to prevent contact of the transplanted cells with $10^{-3}$ mg/ml mitomycin. The mytomycin is used to prevent regrowth of the host RPE. The round piece of the RPE monolayer stabilized in gelatin are folded into a specially-design pipette with a tapered 20 gauge tip for delivery into the subretinal space. The RPE monolayer is loaded into the pipette, and the pipette is introduced through retinotomy. The tissue is injected into the subretinal space using the instrument described in PCT publication WO 96/26759. Freshly isolated RPE cells and RPE cells grown in tissue culture is harvested by trypsinization and loaded into a microsyringe for direct injection into the subretinal space, using a transvitreal approach.

Fluorescein angiography

Fluorescein angiography is performed at day 1, and at 1 and 2 weeks after transplantation surgery. After the induction of anesthesia, the animal's pupil is dilated with 2 drops of 1% mydriacyl and 2.5% phenylephrine. A hand-held KOWA camera with excitation and emission filters matched to the excitation and emission wavelengths of fluorescein is used. Intravenous access is established, and 5ml of sodium fluorescein (10%) is injected intravenously. Fundus photographs are taken with T-max 400 black and white film immediately before fluorescein injection and in rapid sequence after fluorescein injection; late photos are taken 10 minutes after injection.

Histological Examination of Tissue in Gaft Area

Light microscopy

Animals are sacrificed two weeks after recovery from the surgical procedure and the bleb areas and debridement areas are examined by light microscopy and two-dimensional reconstruction of plastic embedded specimens, fluorescence and transmission electron microscopy at 1 hour, 1 and 2 weeks after surgery. The Y chromosome probe is used for in situ hybridization to identify the donor cells in the subretinal space. After sacrificing the animal with a barbiturate overdose, both eyes are rapidly enucleated, the anterior segment is removed, and the posterior pole is immersed in a mixture of 2% glutaraldehyde and 10% formalin in phosphate-buffered saline. The globes are fixed for at least 48 hours, and fixative is then washed out and the globs are stored in sodium cacodylate buffer. Tissue for light microscopy or TEM is washed in phosphate buffer, placed in 1% osmium tetroxide overnight at 4° C., and washed in buffer. Samples are then dehydrated in graded alcohols, stained with 5% uranyl acetate in 100% ethanol, and placed in propylene oxide before embedding in an epoxy resin (LX112, Ladd Research Industries, Burlington, Vt.). One micron sections are cut for light microscopy and stained with toluidine blue. Eight nanometer sections are cut for TEM, placed on copper grids, and stained with 2% uranyl acetate and 0.3% lead citrate before study by TEM.

Y chromosome staining is performed with the in situ probe as described above. The male cells in the graft are identified by nuclear staining, allowing definitive identification of cells from the donor RPE. If cell division has occurred, this is correlated with the donor cell identification to determine whether the fetal cells have expanded in the site of RPE damage. This expansion of cells is particularly important for the repopulation of the central areas of the retina in macular degeneration.

Two dimensional reconstruction of light microscope sections is performed as described in Del Priore (1996) *Mtg. of Assn Vis. & Ophthamol*. Briefly, tissue embedded in plastic is serially sections; every fifth section is numbered sequentially and examined for the presence of retinal pigment epithelium and for integrity of the vascular lumens of the choriocapillaris. The location of the RPE cells are recorded by measuring the distance from the edge of the RPE defect to the margins on the specimen; similar measurements are obtained for the choriocapillaris. In this fashion, two-dimensional maps are constructed showing the location of the RPE defect and corresponding areas of choriocapillaris nonperfusion. If necessary, some sections can be stained for factor-VII related antigens to detect the presence of vascular endothelium of the choriocapillaris.

Confocal microscopy

Confocal microscopy of the choriocapillaris in trephined sections of porcine eye wall is performed, with and without fluorescence labeling of the choriocapillaris endothelium. Flat-mount preparation of RPE, Bruch's membrane, and choriocapillaris in the debrided area are prepared as follows. After RPE debridement, the fixed globes are cleaned of extraocular tissue, and rinsed with buffer. A circumferential incision is made along the or a serrata using a sterior dissecting microscope, the vitreous and neural retain is carefully removed. A cornescleral trephine is used to punch 6–8 mm buttons containing the area of previous RPE debridement. The RPE-Bruch's membrane-choroid complex is carefully separated from the underlying sclera, and placed on glass slides. The tissue specimen is flattened and the excess fluid around the tissue aspirated prior to immunofluorescence staining.

For immunostaining of the extracellular matrix components of Bruch's membrane, non-specific binding sides are blocked by incubating the flat mount with 1% bovine serum albumin in an humidified atmosphere at 37° C. for 30 minutes. The tissue is rinsed three times with phosphate buffered saline (PBS), incubated with the anti-elastin antibody (1:2500) at 37° C. for 1 hour, and stained with an anti-mouse IgG conjugated with fluorescein (maximum absorbance: 495 nm; maximum emission: 525 nm; dilution of 1:128) to label the anti-elastin antibody binding sites (Sigma Immunochemicals, St. Louis, Mo.). The same piece of tissue is then stained with primary mouse antibodies against a different extracellular matrix component of Bruch's membrane; i.e., anti-fibronectin (1:400 dilution), anti-laminin (1:1000), or anti-type IV collagen (1:500) (Sigma); anti-deparan sulfate, anti-vitronectin and antibodies to other collagen subtypes may also be used. The tissue is then incubated with anti-mouse IgG conjugated with cy3 (maximum absorbance: 552 nm; maximum emission: 565 nm; dilution of 1:200) to visualize either fibronectin, laminin, Type IV collagen, or other ECM components. This dual wavelength staining procedure should allow a determination of the distribution of fibronectin, laminin, type IV collagen and other extracellular matrix molecules internal and external to the elastin layer located in the midportion of the Bruch's membrane. A the end of the labeling process the tissue is covered with a glass cover slip and examined with the confocal microscope. Negative controls are unstained tissue, and tissue stained as described above except that non primary antibody is used.

Confocal immunofluorescence microscopy is performed with a Noran Odyssey real-time laser confocal microscope (Middleton, Wis.) with a 300 mW argon laser. The laser is attached to an inverted light microscope (Optiphot-2, Nikon, Japan) and a 40X oil immersion objective with a numerical aperture of 1.3 (Nikon, Japan) is used in all imaging studies. Fluorescein-labeled molecules is excited using the blue argon wavelength (488 nm) and the emission from the fluorescein is collected with a filter that transmits between 520–560 nm. The excitation and barrier filter settings for cy3 are 528.7 nm and $\geq$550 nm, respectively.

Cell Viability and Proliferation

Assayfor live cells

The LIVE/DEAD cell assay is done to determine the viability of the transplanted RPE. After enucleation, the unfixed globe is hemisected at the or a serrata, and the anterior segment, vitreous and neural retina is removed. The area of the transplant is identified by carefully inspecting the transplanted RPE, Bruch's membrane and choroid is prepared as above. The unfixed flat mount preparation is transferred to a cover slip or glass slide and maintained at 37° C. prior to use of the LIVE/DEAD Viability/Cytotoxicity Kit (Molecular Probes, Eugene, Oreg.) which is known to be more sensitive than conventional colorimetric methods. This kit contains two probes: calcein and ethidium homodimer. It relies on intracellular esterase activity which cleaves the calcein and forms a green fluorescent membrane-imperneable product. In dead cells, ethidium can easily pass through the compromised membranes to attach to the DNA, yielding a red fluorescence. At least three different areas containing approximately 250 cells are counted under 100× magnification. The viability of the transplanted RPE sheet is expressesjas the average ratio of live cells to the total number of cells at these three different areas. Confocal microscopy is used to optically isolate the RPE layer if these cells cannot be easily distinguished from the underlying choriocapillaris in the flat mount.

Apoptosis evaluation

In order to determine the number of apoptotic cells among the transplant, the TUNEL (terminal deoxynucleotidyl transferase-mediated dUTP nick end labeling) technique is used to identify the apoptotic cells in the attached and unattached cell populations (Boehringer Mannheim GmbH, Mannheim, Germany). Details of this technique are described in Sgonc et al. (1994) *Trentds Genet.* 10:41–42. Briefly, flat mount preparations are prepared as described above and are fixed and treated with 0.1% Triton x-100 (if necessary) and 0.1% sodium citrate solution for 2 minutes on ice. The tissue is then incubated with a mixture of fluorescein-labeled nucleotides and terminal deoxynucleotidyl transferase (TdT) from calf thymus. Fluorescence microscopy is used to visualize the apoptotic cells at the end of this period. In order to visualize the incorporated fluorescein with phase contrast microscopy, the tissue is incubated for 30 minutes with sheep anti-fluorescein antibody fragments conjugated with alkaline phosphatase. A solution of nitro blue tetrazolium chloride and 5-bromo-4-chloro-3-indolyl-phosphate (NBT/BCIP, Boehringer Mannheim GmbH, Mannheim, Germany) is used as a substrate to visualize the alkaline phosphatase signal. This technique is used to demonstrate apoptosis in RPE cells detached from a substrate in vitro.

Proliferation of fetal cells after transplantation

The proliferative ability of the surviving RPE cells is determined using autoradiography. To determine RPE proliferation in the transplants, autoradiography is performed as described by Smiddy et al. (1986) *Arch. Ophthamol.* 104:1065–1069. Eyes are injected intravitreally with 200 $\mu$Ci of tritiated thymidine in 0.1 ml of PBS three days before the animals are sacrificed. Tissue is then processed for light microscopy as described above. After sectioning, unstained slides with no coverslips are cleaned, demagnetized, and dipped in photographic emulsion under dark conditions (Kodak NTB-s diluted with distilled water 1:1 at 42° C.). Slides are dried overnight and stored in light-free containers for 2–8 weeks. These slides are photographed under phase contrast, and the autoradiographic grains examined and photographed with a standard phase contrast system. The autoradiographs are quantitated by counting the number of cell nuclei at the level of the RPE and choroid showing uptake on the microscope sections. The number of labeled cells is determined by two independent observers.

Example III

Methods of Producing Essentially Pathogen-Free Swine from which Cells of the Invention can be Obtained A. Collecting, Processing, and Analyzing Pig Fecal Samples for Signs of Pathogens Feces are extracted from the pig's rectum manually and placed in a sterile container. About a 1.5 cm diameter portion of the specimen was mixed thoroughly in 10 ml of 0.85% saline. The mixture is then strained slowly through a wire mesh strainer into a 15 ml conical centrifuge tube and centrifuged at 650×g for 2 minutes to sediment the remaining fecal material. The supernatant is decanted carefully so as not to dislodge the sediment. and 10% buffered formalin was added to the 9 ml mark, followed by thorough mixing. The mixture is allowed to stand for 5 minutes. 4 ml of ethyl acetate is added to the mixture and the mixture is capped and mixed vigorously in an inverted position for 30 seconds. The cap is then removed to allow for ventilation and then replaced. The mixture is centrifuged at 500×g for 1 minute (four layers should result: ethyl acetate, debris plug, formalin and sediment). The debris plug is rimmed using an applicator stick. The top three layers are carefully discarded by pouring them off into a solvent container. The debris attached to the sides of the tube is removed using a cotton applicator swab. The sediment is mixed in either a drop of formalin or the small amount of formalin which remains in the tube after decanting. Two separate drops are placed on a slide to which a drop of Lugol's iodine is added. Both drops are coverslipped and carefully examined for signs of pathogens, e.g., protozoan cysts of trophozoites, helminth eggs and larvae. Protozoan cyst identification is confirmed, when required, by trichrome staining.

B. Co-cultivation Assay for Detecting the Presence of Human and Animal Viruses in Pig Cells Materials:

Cell lines

African green monkey kidney, (VERO), cell line American Type Culture Collection, (ATCC CCL81), human embryonic lung fibroblasts, (MRC-5) cell line American Type Culture Collection, (ATCC CCL 171), porcine kidney, (PK-1 5), cell line American Type Culture Collection, (ATCC CRL 33), porcine fetal testis, (ST), cell line American Type Culture Collection, (ATCC CRL 1746).

Medium, Antibiotics, and Other Cells, and Equipment

Fetal calf serum, DMEM, Penicillin 10,000 units/ml, Streptomycin 10 mg/ml, Gentamicin 50 mg,/ml, guinea pig erythrocytes, chicken erythrocytes, porcine erythrocytes, Negative Control (sterile cell culture medium), Positive Controls: VERO and MRC-5 Cells: Poliovirus type 1 attenuated, (ATCC VR-1 92) and Measles virus, Edmonston strain, (ATCC VR-24), PK-1 5 and ST Cells: Swine influenza type A, (ATCC VR-99), Porcine Parvovirus, (ATCC VR-742), and Transmissible gastroenteritis of swine, (ATCC VR-743). Equipment: tissue Culture Incubator, Inverted Microscope, Biological Safety Cabinet.

These materials can be used in a co-cultivation assay (a process whereby a test article is inoculated into cell lines (VERO, MRC-5, PK1 5, and ST) capable of detecting a broad range of human, porcine and other animal viruses). Hsuing, G. D., "Points to Consider in the Characterization of Cell Lines Used to Produce Biologicals" in Diagnostic Virology, 1982 (Yale University Press, New Haven, Conn., 1982).

Experimental Design and Methodology:

A total of three flasks (T25) of each cell line are inoculated with at least 1 ml of test article. Three flasks of each cell line can also be inoculated with the appropriate sterile cell culture medium as a negative control. Positive control viruses are inoculated into three flasks of each cell line. After an absorption period, the inoculate is removed and all flasks incubated at 35–37° C. for 21 days. All flasks are observed at least three times per week for the development of cytopathic effects, (CPE), of viral origin. Harvests are made from any flasks inoculated with the test article that show viral CPE.

At Day 7 an aliquot of supernatant and cells from the flasks of each test article are collected and at least 1 ml is inoculated into each of three new flasks of each cell line. These subcultures are incubated at 35–37° C. for at least 14 days. All flasks are observed and tested as described above.

At Day 7, the flasks from each test article are also tested for viral hemadsorption, (HAd), using guinea pig, monkey and chicken erythrocytes at 2–8° C. and 35–37° C. at 14 days postinoculation.

At Day 21, if no CPE is noted, an aliquot of supernatant from each flask is collected, pooled, and tested for viral hemagglutination, (HA), using guinea pig, monkey, and chicken erythrocytes at 2–8° C. and 35–37° C. Viral identification is based on characteristic viral cytopathic effects (CPE) and reactivity in HA testing.

The test samples are observed for viral cytopathic effects in the following manner: All cultures are observed for viral CPE at least three times each week for a minimum of 21 days incubation. Cultures are removed from the incubator and observed using an inverted microscope using at least 40x magnification. 100x or 200x magnification is used as appropriate. If any abnormalities in the cell monolayers, including viral CPE, are noted or any test articles cause total destruction of the cell monolayer, supernatant and cells are collected from the flasks and samples are subcultured in additional flasks of the same cell line. Samples can be stored at −60° to −80° C. until subcultured. After 7 and 14 days incubation, two blind passages are made of each test article by collecting supernatant and cells from all flasks inoculated with each sample. Samples can be stored at −60° to −80° C. until subcultured.

Hemadsorbing viruses are detected by the following procedure: after 21 days of incubation, a hemadsorption test is performed on the cells to detect the presence of hemadsorbing viruses. The cells are washed 1–2 times with approximately 5 mls of PBS. One to two mls of the appropriate erythrocyte suspension (either guinea pig, porcine, or chicken erythrocytes), prepared as described below, is then added to each flask. The flasks are then incubated at 2–8° C. for 15–20 minutes, after which time the unabsorbed erythrocytes are removed by shaking the flasks. The erythrocytes are observed by placing the flasks on the lowered stage of a lab microscope and viewing them under low power magnification. A negative result is indicated by a lack of erythrocytes adhering to the cell monolayer. A positive result is indicated by the adsorption of the erythrocytes to the cell monolayer.

Hemagglutination testing, described in detail below, is also performed after 21 days of incubation of the subcultures. Viral isolates are identified based on the cell line where growth was noted, the characteristics of the viral CPE, the hemadsorption reaction, and hemagglutination reactions, as appropriate. The test article is considered negative for the presence of a viral agent, if any of the cell lines used in the study demonstrate viral, CPE, HA, or HAd in a valid assay.

C. Procedure for Preparing and Maintaining Cell Lines used to Detect Viruses in Pig Cells Materials:

Fetal calf serum (FCS), DMEM, Penicillin 10,000 unit/ml, Streptomycin 10 mg/ml, Gentamicin 50 mg/ml, T25 tissue culture flasks, tissue culture incubator (5% $CO_2$, 37° C.)

Procedure:

Aseptic techniques are followed when performing inoculations and transfers. All inoculations and transfers are performed in a biological safety cabinet. Media is prepared by adding 10% FCS for initial seeding, 5% FCS for maintenance of cultures, as well as 5.0 ml of penicillin/streptomycin and 0.5 ml of gentamicin per 500 ml media. Sufficient media is added to cover the bottom of a T25 tissue culture flask. The flask is seeded with the desired cell line and incubated at 37° C., 5% $CO_2$ until cells are 80 to 100% confluent. The flasks are then inoculated with virus (QCP25).

D. Preparation of Erythrocyte (rbc) Suspensions used in Hemadsorption (HAd) and Hemagglutination (HA) Virus Detection Testing Materials:

Phosphate buffered saline, (PBS), pH 7.2, guinea pig erythrocytes stock solution, porcine erythrocytes stock solution, chicken erythrocytes stock solution, sterile, disposable entrifuge tubes, 15 or 50 ml Laboratory centrifuge.

Procedure:

An appropriate amount of erythrocytes (rbc) is obtained from stock solution. The eythrocytes are washed 3 times with PBS by centrifugation at approximately 1000×g for 10 minutes. A 10% suspension is prepared by adding 9 parts of PBS to each one part of packed eythrocytes. The 10% rcb suspensions are stored at 2–8° C. for no more than one week. 0.5% ecb suspensions are prepared by adding 19 parts of PBS to each one part of 10% rbc suspension. Fresh 0 5% rbc suspensions are prepared prior to each day's testing.

Hemagglutination (HA) test

A hemagglutination test is a test that detects viruses with the property to agglutinate erythrocytes, such as swine influenza type A, parainfluenza, and encephalomyocarditis viruses, in the test article. Hsuing, G. D. (1982) Diagnostic Virology (Yale University Press, New Haven, Conn.);. Stites, Daniel P and Terr, Abba I, (1991), Basic and Clinical Immunology (Appleton & Lange, East Norwalk, Conn.).

Materials:

Supernatants from flasks of the VERO cell line, MRC-5 inoculated with the test article, flasks of positive and negative controls, phosphate buffered saline (PBS), pH 7.2, guinea pig erythrocytes (GPRBC), 0.5% suspension in PBS, chicken erythrocytes (CRBC), 0.5% suspension in PBS, porcine erythrocytes (MRBC), 0.5% suspension in PBS Procedure:

All sample collection and testing is performed in an approved biological safety cabinet. 0.5% suspensions of each type of erythrocytes are prepared as described above. The HA test on all cell lines inoculated with samples of the test articles at least 14 days post-inoculation. Positive and negative control cultures are included for each sample and monolayers are examined to ensure that they are intact prior to collecting samples.

At least 1 ml of culture fluid from each flask inoculated with the test article is collected and pooled. 1 ml samples from the negative and positive control cultures are also collected and pooled. A set of tubes is labeled with the sample number and type of erythrocyte (distinguish positive and negative suspension) to be added. Racks may be labeled to differentiate the type of erythrocyte. 0.1 ml of sample is added to each tube. 0.1 ml of the appropriate erythrocyte suspension is added to each tube. Each tube is covered with parafilm and mixed thoroughly. One set of tubes is incubated at 2–8° C. until tight buttons form in the negative control in about 30–60 minutes. Another set of tubes is incubated at 35–37° C. until tight buttons form in the negative control in about 30–60 minutes.

Formation of a tight button of erythrocytes indicates a negative result. A coating of the bottom of the tube with the erythrocytes indicates a positive result.

E. Methods used for Fluorescent Antibody Stain of Cell Suspensions Obtained from Flasks used in Detection of Viruses in Porcine Cells using Cell Culture Techniques (as described in Sections B and C)

Materials:

Pseudorabies, parvovirus, enterovirus. adenovirus, transmissible Gastroenteritis Virus. bovine viral diarrhea, encephalomyocarditis virus, parainfluenza, vesicular stomatitis virus., microscope slides, PBS, incubator with humidifying chamber at 36° C., Evan's blue coutner stain, DI Water, fluorescent microscope, trypsin, serum containing media, acetone, T25 Flask.

Procedure:

Cells (described in Sections B and C) are trypsinized to detach them from the T25 flask and sufficient media is added to neutralize trypsin activity. A drop of cell suspension is placed on each microscope slide and allowed to air dry. A slide for each fluorescent antibody is prepared. Cells are fixed by immersion in acetone for five minutes. Each fluorescent antibody solution is placed on each slide to cover cells and the slides are incubated in humidifying chamber in incubator at 36° C. for 30 minutes. The slides are then washed in PBS for five minutes. The wash is repeated in fresh PBS for five minutes followed by a rinse with DI water.

The cells are counterstained by placing Evan's blue solution on each slide to cover cells for five minutes at room temperature. The slides are then washed in PBS for five minutes. The wash is repeated in fresh PBS for five minutes followed by a rinse with DI water. The slides are then allowed to air dry. Each slide is inspected under a fluorescent microscope. Any fluorescent inclusion bodies characteristic of infection are considered a positive result for the presence of virus.

F. Procedures for Defining Bacteremic Pigs

Materials:

Anaerobic BMB agar (5% sheep blood, vitamin K and hemin [BMB/blood]), chocolate Agar with Iso Vitalex, Sabaroud dextrose agar/Emmons, 70% isopropyl alcohol swabs, betadine solution, 5% $CO_2$ incubator at 35–37° C., anaerobic blood agar plate, gram stain reagents (Columbia Broth Media), aerobic blood culture media (anaerobic brain heart infusion with vitamin K& hemin), septicheck media system, vitek bacterial identification system, laminar flow hood, microscope, and bacteroids and Bacillus stocks Procedure:

Under a larninar flow hood, disinfect the tops of bottles for aerobic and anaerobic blood cultures of blood obtained from pig with 70% isopropyl alcohol, then with betadine The rubber stopper and cap from the aerobic blood culture bottle are removed and a renal septicheck media system is attached to the bottle. The bottles are incubated in 5% $CO_2$ for 21 days at 35–37° C., and observed daily for any signs of bacterial growth (i.e. gas bubbles, turbidity, discoloration or discrete clumps). Negative controls consisting of 5 cc of sterile saline in each bottle and positive controls consisting of Bacillus subtilis in the aerobic bottle and Bacteriodes Vulgaris in the anaerobic bottle are used. If signs of bacterial growth are observed, a Gram stain is prepared and viewed microscopically at 100× oil immersion for the presence of any bacteria or fungi. The positive bottles are then subcultured onto both chocolate agar plates with Iso Vitlex and onto BMB plates. The chocolate plate is incubated at 35–37° C. in 5% $CO_2$ for 24 hours and the BMB anaerobically at 35–37° C. for 48 yeast or fungi that is in evidence at gram stain is subcultured onto a Sabaroud dextrose/Emmons plate. The Vitek automated system is used to identify bacteria and yeast. Fungi are identified via their macroscopic and microscopic characteristic. If no signs of growth are observed at the end of 21 days, gram stain is prepared and observed microscopically for the presence of bacteria and fungi.

Absence of growth in the negative control bottles and presence of growth in the positive control bottles indicates a valid test. The absence of any signs of growth in both the aerobic and anaerobic blood culture bottles, as well as no organisms seen on gram stain indicates a negative blood culture. The presence and identification of microorganism(s) in either the aerobic or anaerobic blood culture bottle indicates of a positive blood culture; this typically is due to a bacteremic state.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A transplantable composition for use in a subject comprising an isolated population of retinal cells obtained from a fetal pig between about days 50 and 70 of gestation.

2. The composition of claim 1, wherein the retinal cells are selected from the group consisting of retinal pigment epithelial cells, neural retina cells and iris epithelial cells.

3. The composition of claim 1, wherein the retinal cells are retinal pigment epithelial cells.

4. The composition of claim 1, wherein the retinal cells are neural retinal cells.

5. The composition of claim 4, wherein the neural retinal cells are rod cells.

6. The composition of claim 4, wherein the neural retinal cells are cone cells.

7. The composition of claim 1, wherein the cells are obtained from a fetal pig between about days 60 and 70 of gestation.

8. The composition of claim 7, wherein the cells are obtained from a fetal pig between days 60 and 65 of gestation.

9. A transplantable composition for use in a subject comprising an isolated population of retinal cells obtained from a fetal pig between about days 50 and 70 of gestation, wherein the cells, in unmodified form, have at least one antigen on the surface of the cells which is capable of stimulating an immune response against the cells in a subject, wherein the antigen on the surface of the cells is altered to inhibit rejection of the cells when introduced into the subject.

10. The composition of claim 9, wherein the antigen on the surface of the cells is contacted prior to transplantation with at least one molecule which binds to the antigen to inhibit rejection of the cells when transplanted into the subject.

11. The composition of claim 10, wherein the antigen on the surface of the cells which is altered is an MHC class I antigen.

12. The composition of claim 11, wherein the cells are contacted prior to transplantation into the subject with at least one anti-MHC class I antibody, or fragment or derivative thereof, which binds to the MHC class I antigen on the surface of the cells but does not activate complement or induce lysis of the cells.

13. The composition of claim 12, wherein the anti-MHC class I antibody is an anti-MHC class I $F(ab')_2$ fragment.

14. The composition of claim 13, wherein the anti-MHC class I $F(ab')_2$ fragment is a $F(ab')_2$ fragment of a monoclonal antibody PT85.

15. The composition of claim 1, further comprising a pharmaceutically acceptable carrier.

16. The composition of claim 1, wherein the cells are obtained from a pig predetermined to be free from at least two organisms which originate in pig and which are capable of transmitting infection or disease to the subject wherein the organisms are selected from the group consisting of parasites, bacteria, mycoplasma and viruses.

17. The composition of claim 3, wherein the retinal pigment epithelial cells are within an intact sheet.

* * * * *